US 9,551,688 B2
(12) United States Patent
Ikushima

(10) Patent No.: US 9,551,688 B2
(45) Date of Patent: Jan. 24, 2017

(54) PROPERTY MEASURING DEVICE FOR OBJECT TO BE MEASURED AND PROPERTY MEASURING METHOD FOR OBJECT TO BE MEASURED

(75) Inventor: Kenji Ikushima, Tokyo (JP)

(73) Assignee: TOKYO UNIVERSITY OF AGRICULTURE AND TECHNOLOGY, Tokyo (JP)

( * ) Notice: Subject to any disclaimer, the term of this patent is extended or adjusted under 35 U.S.C. 154(b) by 484 days.

(21) Appl. No.: 14/233,696

(22) PCT Filed: Jul. 10, 2012

(86) PCT No.: PCT/JP2012/067575
§ 371 (c)(1),
(2), (4) Date: Jan. 17, 2014

(87) PCT Pub. No.: WO2013/011869
PCT Pub. Date: Jan. 24, 2013

(65) Prior Publication Data
US 2014/0150555 A1 Jun. 5, 2014

(30) Foreign Application Priority Data

Jul. 20, 2011 (JP) .................................. 2011-158637

(51) Int. Cl.
*G01N 9/04* (2006.01)
*G01N 27/72* (2006.01)
(Continued)

(52) U.S. Cl.
CPC .......... *G01N 27/725* (2013.01); *G01N 29/043* (2013.01); *G01N 29/2418* (2013.01); *G01N 29/2431* (2013.01); *G01N 29/346* (2013.01)

(58) Field of Classification Search
CPC G01N 27/725; G01N 29/043; G01N 29/2418; G01N 29/346; G01N 29/2431
See application file for complete search history.

(56) References Cited

U.S. PATENT DOCUMENTS 3,809,070 A * 5/1974 Doll ..................... A61B 5/0265
600/409
4,309,905 A * 1/1982 Maizenberg ......... G01N 27/725
324/227
(Continued)

FOREIGN PATENT DOCUMENTS

JP S57-51895 B2 3/1982
JP 05-039619 B2 2/1993
(Continued)

OTHER PUBLICATIONS

International Search Report, mailed Oct. 2, 2012, for PCT/JP2012/067575, 4 pages.
(Continued)

*Primary Examiner* — Harshad R Patel
*Assistant Examiner* — Samir M Shah
(74) *Attorney, Agent, or Firm* — Seed IP Law Group LLP

(57) ABSTRACT

[Problem to be Solved] To provide a property measuring device for measuring a measurement object, which can highly reliably extract an electric signal serving as the measurement object from an electromagnetic field noise or the like generated by an acoustic wave generating source even if the acoustic wave is a continuous wave, while a high spatial resolution is maintained, by using an acoustic wave as a properly measuring means for measuring an object and method thereof.

[Means for Solving the Problem] A property measuring device 100 for measuring a measurement object of the present invention includes: an acoustic wave emitting portion 40 arranged away from a measurement object 90 and emitting an amplitude-modulated acoustic wave; a receiver 50 for receiving an electromagnetic field generated when the acoustic wave is emitted to the measurement object 90; and a measuring portion 60 for extracting at least one type of properties selected from a group consisting of an electric (Continued)

property, a magnetic property, an electromechanical property, and a magnetomechanical property of the measurement object 90, based on at least one measurement selected from a group consisting of measurements of a strength, a phase, and a frequency of the electromagnetic field.

19 Claims, 9 Drawing Sheets

(51) Int. Cl.
*G01N 29/04* (2006.01)
*G01N 29/24* (2006.01)
*G01N 29/34* (2006.01)

(56) References Cited

U.S. PATENT DOCUMENTS

| | | | | |
|---|---|---|---|---|
| 5,168,224 | A * | 12/1992 | Maruizumi | G01N 23/04 324/300 |
| 5,170,666 | A * | 12/1992 | Larsen | G01N 29/2418 73/571 |
| 7,165,451 | B1 * | 1/2007 | Brooks | A61B 5/0093 601/2 |
| 2002/0035327 | A1 * | 3/2002 | Kruger | A61B 5/0091 600/437 |
| 2002/0050815 | A1 * | 5/2002 | Suzuki | G01R 33/24 324/248 |
| 2003/0133596 | A1 * | 7/2003 | Brooks | G06K 9/00 382/115 |
| 2003/0230344 | A1 * | 12/2003 | Ellson | B01L 3/0268 137/391 |
| 2005/0046858 | A1 * | 3/2005 | Hanson | G01B 11/0675 356/457 |
| 2007/0135984 | A1 * | 6/2007 | Breed | B60R 21/01516 701/45 |
| 2009/0221900 | A1 * | 9/2009 | Ikushima | A61B 5/0093 600/409 |

FOREIGN PATENT DOCUMENTS

| | | |
|---|---|---|
| JP | 2000-023947 A | 1/2000 |
| JP | 2011-104241 A | 6/2011 |
| WO | 2007-055057 A1 | 5/2007 |

OTHER PUBLICATIONS

Beaurepaire et al., "Coherent terahertz emission from ferromagnetic films excited by femtosecond laser pulses," Applied Physics Letters 84(18):3465-3467, May 3, 2004.

Naito et al., "Measurements of acoustically stimulated electromagnetic response by an amplitude-modulation method," Extended Abstracts, Japan Society of Applied Physics and Related Societies, Mar. 2012, 3 pages.

* cited by examiner

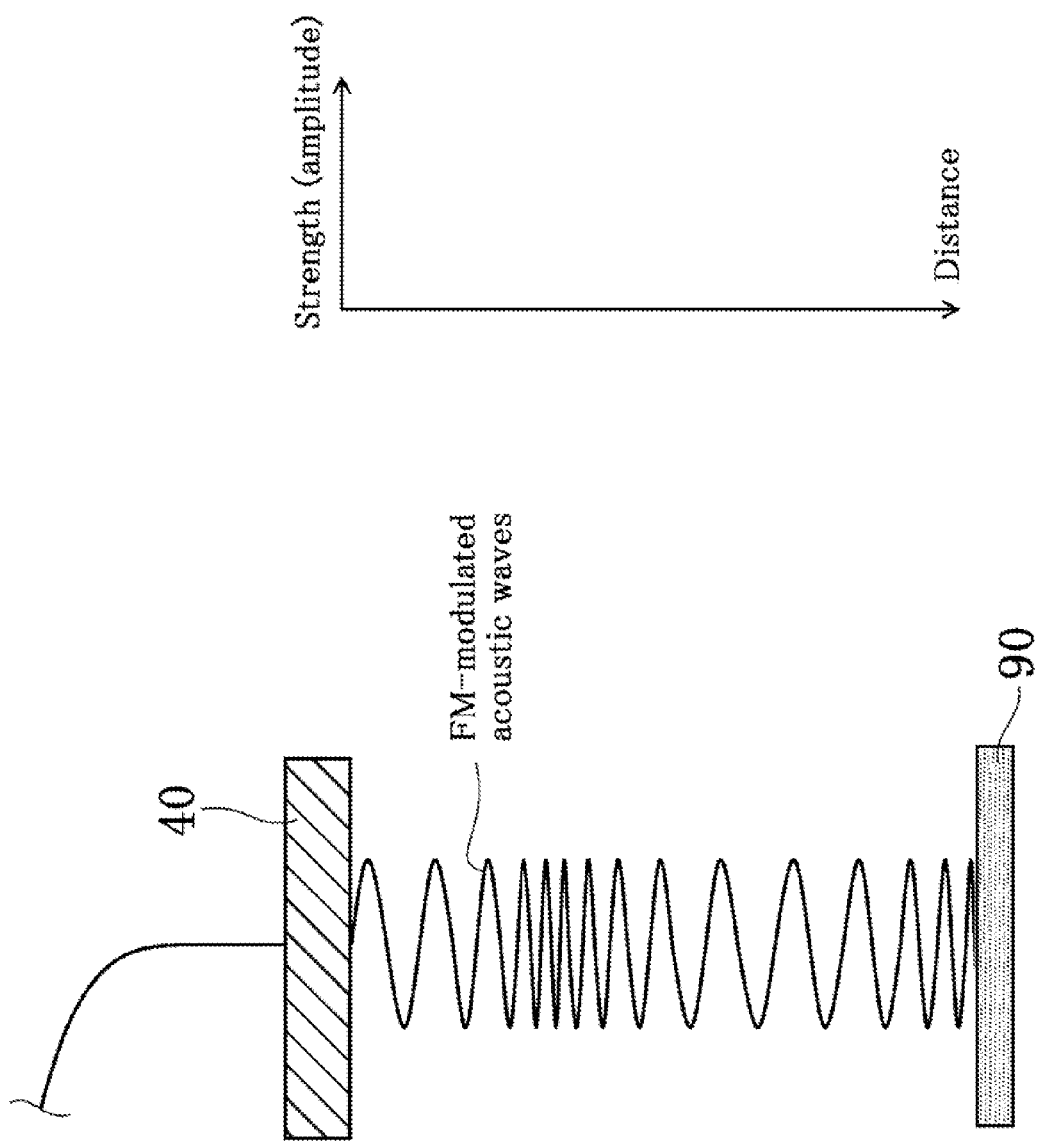

PROPERTY MEASURING DEVICE FOR OBJECT TO BE MEASURED AND PROPERTY MEASURING METHOD FOR OBJECT TO BE MEASURED

TECHNICAL FIELD

The present invention relates to a property measuring device for measuring an object which is applicable to an object that can generate (can radiate) an electromagnetic field by receiving an amplitude-modulated or frequency-modulated acoustic wave, and a method thereof.

BACKGROUND ART

Non-Patent Document 1 reports that, when magnetization of a ferromagnetic thin film is time-modulated, radiation of a coherent terahertz electromagnetic wave is observed. However, the technique described in Document 1 merely discloses magnetized modulation not by emitting an acoustic wave, but by emitting femtosecond laser light.

In addition, measurement by an acoustic wave (typically, supersonic wave) is also popularly used as a non-destructive inspection of various structures. This is because the acoustic wave has an advantage of having a high internal transmittance for an object such as a metal or a concrete block through which transmission of light is usually difficult. However, the use of such an acoustic wave has been limited to inspections or diagnoses of a mass density distribution and elastic property of a measurement object.

Under the aforementioned circumstances, the inventor of the present invention proposes a property measuring device for measuring a measurement object by an acoustically stimulated electromagnetic field which is applicable to various types of objects as measurement objects, and a method thereof (Patent Document 1).

PRIOR ART DOCUMENTS

Patent Document

Patent Document 1: WO2007/055057 A

Non-Patent Document

Non-Patent Document 1: E. Beaurepaire et al. (other five persons), "Appl. Phys. Lett.", Vol. 84, No. 18, pp. 3465-3467, 3 May 2004

SUMMARY OF THE INVENTION

Problems to be Solved by the Invention

The excellent point of the property measuring device and the method thereof for measuring the object created by the inventor of the present invention is that an acoustic wave having a high internal transmittance is used generation of an electromagnetic field having a frequency identical with that of the emitted acoustic wave (typically RF wave-microwave) is actively promoted through dipole radiation or the like, and the electric and/or magnetic properties are measured. Here, since Patent Document 1 already discloses detailed descriptions about the principle for realizing the property measuring method for measuring the object, the description thereof will not be repeated. However, the one that is particularly notable is that, because of a difference in the speeds of sound and light, the acoustic wave, as compared with the electromagnetic wave, has a wavelength shorter by five digits of magnitudes at an identical frequency. For this reason, it is possible to realize focusing in the order of millimeters and micrometers in the frequency band of MHz and GHz in which a real-time waveform can be easily obtained. This means that, since the acoustic wave measurement can increase the spatial resolution by (for example) five digits at an identical frequency as compared with the electromagnetic measurement, superiority of the property measuring device and the method thereof for measuring the object can be exerted.

Incidentally, the property measuring device and the method thereof for measuring the object has a remarkable advantage that, if a pulsed acoustic wave is emitted, an electric signal to be measured can be measured while it is temporally separated (extracted, in another word) from the electromagnetic field noise or the like generated by an acoustic wave generating source. However, when the means for measuring the properties of an object was performed by emitting a continuous wave, it was not necessarily easy to highly reliably extract the electric signal from the electromagnetic field noise or the like generated by the acoustic wave generating source. The problem of the continuous wave becomes apparent when, for example, an echo of the acoustic wave emitted to the electromagnetic noise caused by the acoustic wave generating source or a measurement object is present by accidentally overlapping the electromagnetic fields generated by the object (measurement object). The reason for this is that a frequency of the acoustic wave generated by the acoustic wave generating source and a frequency of a signal to be measured belong to the same frequency band.

In addition, also in the case where a pulsed acoustic wave from which the signal to be measured can be extracted in a relatively easier manner is emitted, there is a problem in which a measurement time becomes longer since an effective integral time is shorter. Specifically, for example, a time width generated by the signal to be measured is generally ten microseconds or shorter, whereas a repeating cycle of the pulsed acoustic wave is normally 0.1 seconds (100 Hz). For this reason, a time required for effectively integrating the signal is merely 0.01% of the measuring time. To state it differently, a signal strength ratio with respect to a noise strength ratio obtained by integrating for one second (signal-to-noise ratio, hereinafter simply referred to as "S/N ratio") becomes considerably smaller.

Solutions to the Problems

The present invention makes a great contribution to further improvement of a property measuring technique for measuring a measurement object, which can highly reliably extract an electric signal serving as the measurement object from an electromagnetic field noise or the like generated by the acoustic wave generating source even if the acoustic wave is a continuous wave, while a high spatial resolution is maintained, by using an acoustic wave as a property measuring means for measuring an object.

As described above, if a frequency of the electromagnetic noise or the like generated by the acoustic wave generating source and an frequency of the electric signal serving as the measurement object belong to an identical frequency band, it is difficult to appropriately extract the electric signal serving as the measurement object from the noise particularly when the acoustic wave is emitted as a continuous wave. In contrast, by emitting a pulsed acoustic wave, although the measurement accuracy is increased, it is not easy to make a measurement in a short period of time. The inventor of the present invention made a diligent study in such a so-called paradoxical situation and, as a result, found that the plurality of problems described above could be solved simultaneously by adding a creative idea different from the conventional one to the acoustic wave for emitting, and made the present invention.

A property measuring device for measuring a measurement object of the present invention includes: an acoustic wave emitting portion arranged away from the measurement object and emitting an amplitude-modulated or frequency-modulated acoustic wave; a receiver for receiving an electromagnetic field generated when the acoustic wave is emitted to the measurement object; and a measuring portion for extracting at least one type of properties selected from a group consisting of an electric property, a magnetic property, an electromechanical property, and a magnetomechanical property of the measurement object, based on at least one measurement selected from a group consisting of measurements of a strength, a phase, and a frequency of the electromagnetic field.

According to this property measuring device, since the acoustic wave emitted from the acoustic wave emitting portion is the amplitude-modulated acoustic wave or the frequency-modulated acoustic: wave, extraction of the electromagnetic field generated by the measurement object becomes easier as compared with the case where the acoustic wave is not amplitude-modulated or frequency-modulated. To state it differently, according to this property measuring device, it is possible to highly reliably extract the electric signal to be measured from the electromagnetic field noise or the like generated by the acoustic wave generating source. In addition, according to this property measuring device, the acoustic wave emitting portion is arranged away from the measurement object as described above, and therefore it is advantageous in the sense that the device can be utilized as a non-destructive measuring device.

Incidentally, in the property measuring device for measuring the measurement object described above, it is a preferable aspect that the acoustic wave emitting portion continuously generates the amplitude-modulated or frequency-modulated acoustic wave. When the acoustic wave that is emitted is a continuous wave, it becomes easy to extract the electromagnetic field generated by the measurement object, and in addition a time required for effectively integrating the signal increases significantly. As a result, the S/N ratio is drastically improved, and the measurement time required when the continuous wave is emitted can be noticeably shortened as compared with the case where the pulsed acoustic wave is emitted.

Further, a property measuring method for measuring a measurement object of the present invention includes the steps of emitting an amplitude-modulated or frequency-modulated acoustic wave to the measurement object; receiving an electromagnetic, field generated by the measurement object; and measuring which extracts at least one type of properties selected from a group consisting of an electric property, a magnetic property, an electromechanical property, and a magnetomechanical property of the measurement object, based on at least one measurement selected from a group consisting of measurements of a strength, a phase, and a frequency of the electromagnetic field.

According to this property measuring method, since the acoustic wave to be emitted is the amplitude-modulated acoustic wave or the frequency-modulated acoustic wave, extraction of the electromagnetic field generated by the measurement object becomes easier as compared with the case where the acoustic wave is not amplitude-modulated or frequency-modulated. To state it differently, according to this property measuring method, it is possible to highly reliably extract the electric, signal to be measured from the electromagnetic field noise or the like generated by the acoustic wave generating source.

Incidentally, in the property measuring method for measuring the measurement object described above, it is a preferable aspect that the acoustic wave is a continuous amplitude-modulated or frequency-modulated acoustic wave. When the acoustic wave that is emitted is a continuous wave, it becomes easy to extract the electromagnetic field generated by the measurement object, and in addition a time required for effectively integrating the signal increases significantly. As a result, the S/N ratio is drastically improved, and the measurement time required when the continuous wave is emitted can be noticeably shortened as compared with the case where the pulsed acoustic wave is emitted.

Further, a property measuring program for measuring a measurement object of the present invention includes the steps of: emitting an amplitude-modulated or frequency-modulated acoustic wave to the measurement object; receiving an electromagnetic field generated by the measurement object; and measuring which extracts at least one type of properties selected from a group consisting of an electric property, a magnetic property, an electromechanical property, and a magnetomechanical property of the measurement object, based on at least one measurement selected from a group consisting of measurements of a strength, a phase, and a frequency of the electromagnetic field.

By executing this property measuring program, extraction of the electromagnetic field generated by the measurement object becomes easier as compared with the case where the acoustic wave is not amplitude-modulated or frequency-modulated, since the acoustic wave to be emitted is the amplitude-modulated acoustic wave or the frequency-modulated acoustic wave. To state it differently, according to this property measuring program, it is possible to highly reliably extract the electric signal to be measured from the electromagnetic field noise or the like generated by the acoustic wave generating source.

It should be noted that, in the present application, an electromagnetic signal (RF signal) flowing through a cable and an amplifier is referred to as "electric signal" for convenience sake. In addition, in the present application, an electromagnetic field (RE field) generated in a medium between the acoustic wave emitting portion and the measurement object is referred to as "electromagnetic field" for convenience sake. Further, although the "electromagnetic field" may be referred to as the "electromagnetic wave", the present application uses an expression of the "electromagnetic field" which indicates a concept including both so-called near-field and far-field, which was conventionally intended by the inventor of the present invention and the applicant of the present application.

Effects of the Invention

According to a property measuring device for measuring a measurement object of the present invention, extraction of the electromagnetic field generated by the measurement object becomes easier as compared with the case where the acoustic wave is not amplitude-modulated or frequency-modulated, since the acoustic wave to be emitted from the acoustic wave emitting portion is the amplitude-modulated acoustic wave or the frequency-modulated acoustic wave. To state it differently, according to this property measuring device, it is possible to highly reliably extract the electric signal to be measured from the electromagnetic field noise or the like generated by the acoustic wave generating source.

In addition, according to a property measuring method for measuring a measurement object of the present invention, since the acoustic wave to be emitted is the amplitude-modulated acoustic wave or the frequency-modulated acoustic wave, extraction of the electromagnetic field generated by the measurement object becomes easier as compared with the case where the acoustic wave is not amplitude-modulated or frequency-modulated. To state it differently, according to this property measuring method, it is possible to highly reliably extract the electric signal to be measured from the electromagnetic field noise or the like generated by the acoustic wave generating source.

Further, by executing a property measuring program for measuring a measurement object of the present invention, extraction of the electromagnetic field generated by the measurement object becomes easier as compared with the case where the acoustic wave is not amplitude-modulated or frequency-modulated, since the acoustic wave to be emitted is the amplitude-modulated acoustic wave or the frequency-modulated acoustic wave. To state it differently, according to this property measuring program, it is possible to highly reliably extract the electric signal to be measured from the electromagnetic field noise or the like generated by the acoustic wave generating source.

BRIEF DESCRIPTION OF THE DRAWINGS

FIG. 9 is a conceptual diagram depicting a relationship between an acoustic wave generator and the measurement object in the property measuring device for measuring a measurement object according to the other embodiment of the present invention.

DESCRIPTION OF REFERENCE SIGNS

Figure 1:
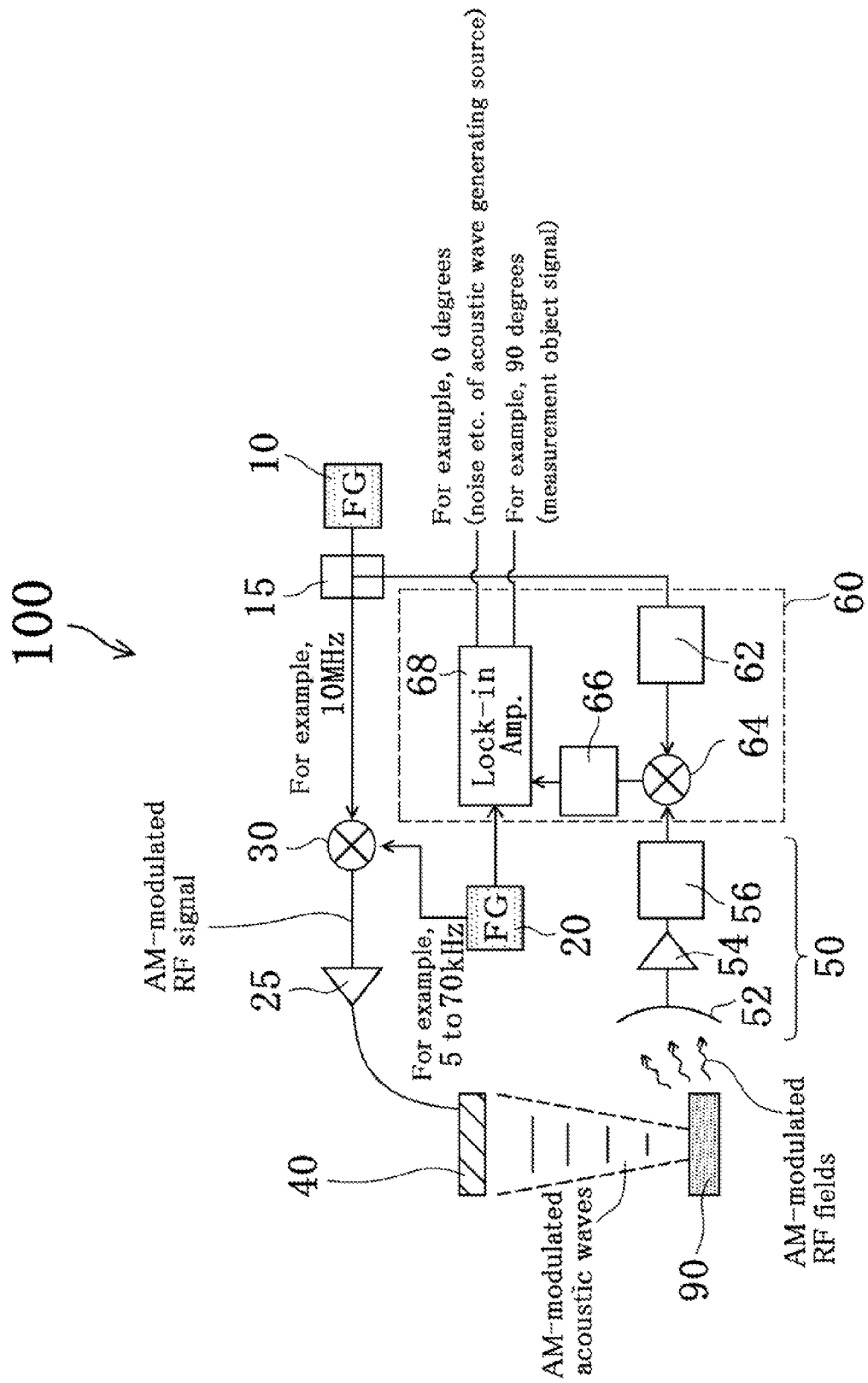
FIG. 1 is a configuration diagram of a property measuring device for measuring a measurement object according to a first embodiment of the present invention.

1 Acoustic wave focused beam
2 Acoustic wave focused region
3 Positively charged particles
4 Negatively charged particles
5 Vibration direction of acoustic wave
6 Electromagnetic field stimulated by acoustic wave
10 First waveform generator
15 Distributor
20 Second waveform generator
25 First amplifier
30 First mixer
40 Acoustic wave generator
50, 70, 80 Receiver
52 Antenna
54 Second amplifier
56 Band-pass filter
60 Measuring portion
62 Phase shifter
64 Second mixer
66 Low-pass filter
68 Lock-in amplifier
72 Resonance circuit
74, 84 Amplifier
82a Front surface electrode
82b Back surface electrode
90 Measurement object
100, 200, 300, 400 Property measuring device for measuring measurement object
412 Frequency modulation and oscillation circuit
467 Frequency modulation and demodulation circuit

EMBODIMENTS OF THE INVENTION

Next, embodiments of the present invention will be described in details with reference to the accompanying drawings. In the description, a portion common to one another in the entire drawings is identified by an identical reference symbol. In addition, the elements in the embodiments are not illustrated in accordance with an actual ratio of sizes.

First Embodiment

FIG. 1 is a configuration diagram of a property measuring device 100 for measuring a measurement object according to this embodiment (hereinafter, simply referred to as "property measuring device 100"). Since the drawing is a schematic drawing, a controller for controlling each configuration portion and/or peripheral equipment or a peripheral device including a computer connected to each configuration portion and the controller is not illustrated in FIG. 1. The same is also applied to the drawings illustrating configurations of a property measuring device for measuring a measurement object different from that of this embodiment in the present application.

As illustrated in FIG. 1, the property measuring device 100 according to this embodiment is broadly divided into three configuration portions.

First, a first configuration portion is an acoustic wave generator 40 for generating an acoustic wave emitted to a measurement object 90. In this embodiment, an amplitude of the acoustic wave to be emitted is modulated. Specifically, first, a waveform of a high-frequency wave (frequency of 10 MHz in this embodiment) generated by a first waveform generator (FG) 10 passes through a distributor 15, and is synthesized with a waveform generated by an additional second waveform generator 20 for generating a low-frequency (frequency of 5 kHz to 70 kHz in this embodiment) by a DBM (Double-Balanced Mixer) 30 to form a waveform whose amplitude is modulated. Then, in this embodiment, after the modulated waveform is amplified by a first amplifier 25, the measurement object 90 is irradiated, by the acoustic wave generator 40, with the amplitude-modulated acoustic wave whose carrier frequency ($f_0$) is 10 MHz, and a modulation frequency of amplitude modulation (hereinafter, also referred to as "amplitude modulation frequency") ($f_m$) is 5 kHz to 70 kHz. Here, as described above, an acoustic wave emitting portion according to this embodiment only refers to the acoustic wave generator 40 in a narrow sense, but the acoustic wave emitting portion according to this embodiment includes the first waveform generator 10, the second waveform generator 20, the first mixer 30, the first amplifier 25 in addition to the acoustic wave generator 40 in a broad sense.

Incidentally, if the acoustic wave emitting portion (e.g., the acoustic wave generator 40) of the property measuring device 100 is away from the measurement object 90, a distance therebetween is not particularly restricted. To be more specific, if a medium not causing any electromagnetic field which is equal to or larger than an electromagnetic field to be measured and which is stimulated by the acoustic wave is interposed between the acoustic wave emitting portion (e.g., the acoustic wave generator 40) and the measurement object 90, the distance between the acoustic wave emitting portion and the measurement object 90 is not particularly restricted. It should be noted that, in the present application, the amplitude modulation may be simplified as "AM".

Here, the waveform that is amplitude-modulated before being emitted by the acoustic wave generator 40 is amplified by the first amplifier 25. However, this embodiment is not restricted to this configuration. For example, if an acoustic wave intensity required for the measurement is generated even in the case where the first amplifier 25 is absent, it is confirmed that substantially the same effect or at least part thereof is provided as in the case of the property measuring device 100 according to this embodiment.

Next, a second configuration portion is a receiver 50 for receiving an electromagnetic field including a measurement object signal (hereinafter, also simply referred to as "electromagnetic field") generated by the measurement object 90 when the amplitude modulated acoustic wave is emitted to the measurement object 90.

Since Patent Document 1 described above carries a detailed description thereof, a description of an electromagnetic field stimulated in a portion irradiating the measurement object 90 with the acoustic wave will be given here.

Figure 2:
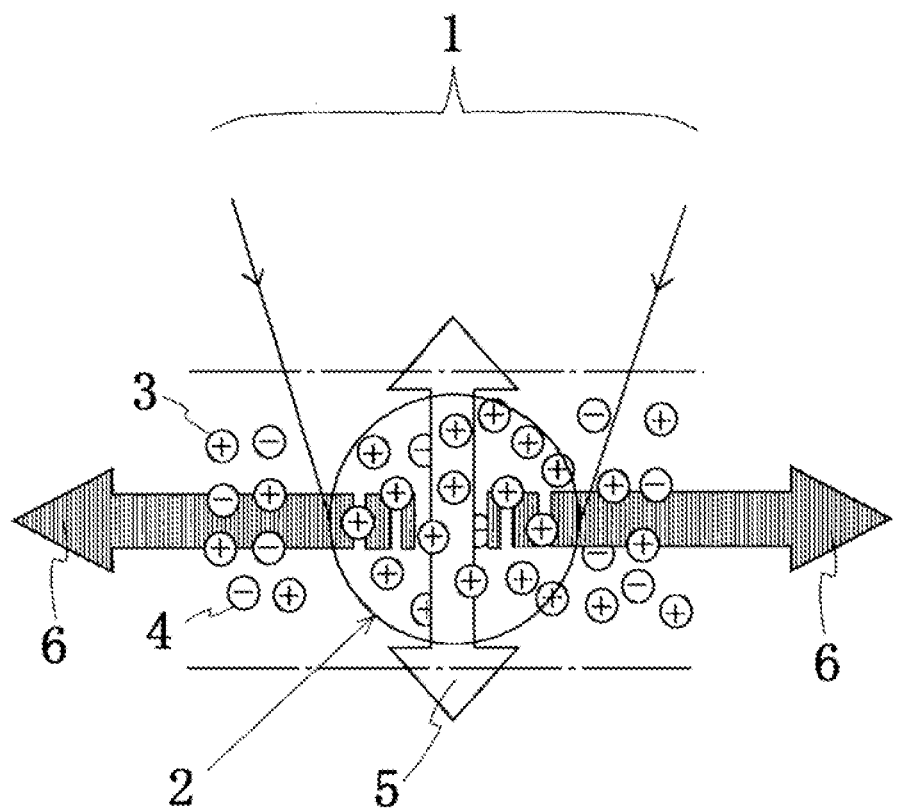
FIG. 2 is a diagram illustrating a state of an electromagnetic field stimulated by emitting an acoustic wave to a part of an object.

FIG. 2 is a diagram illustrating a state of an electromagnetic field stimulated by irradiating a part of the measurement object 90 with the acoustic wave. FIG. 2 illustrates a state in which an acoustic wave focused beam 1 is focused on a portion 2 of the measurement object 90, and symbols with circled + and − respectively indicate positively charged particles 3 and negatively charged particles 4. In an acoustic wave focused region 2 of the measurement object 90, concentrations between the positively charged particles 3 and the negatively charged particles 4 are out of balance, and therefore a state of a charge distribution in which the positively charged particles 3 outnumber the negatively charged particles 4 is illustrated. In addition, an arrow 5 indicates an acoustic wave vibration direction of the acoustic wave focused beam 1, which corresponds to a direction of the electromagnetic field. Further, an arrow 6 indicates a magnetic field generated in a plane perpendicular to the arrow 5.

As illustrated in FIG. 2, by emitting the acoustic wave focused beam 1, the positively charged particles 3 and the negatively charged particles 4 vibrate at a vibration frequency of the acoustic wave in a vibration direction (arrow 5) of the acoustic wave. Then, since the vibrations of the positively charged particles 3 and the negatively charged particles 4 mean that the charges vibrate, magnetic fields (arrow 6) generated in the plane perpendicular to the vibration direction 5 are stimulated. The electromagnetic fields thus generated have phases that are deviated by $\pi$ from each other, these electromagnetic fields cancel each other, and, as a result, the electromagnetic fields are not stimulated. However, the acoustic wave focused region 2 of the measurement object 90 has a charge distribution state in which the positively charged particles 3 outnumber the negatively charged particles 4. Accordingly, they cannot cancel each other entirely, and the net electromagnetic, field (arrow 6) is stimulated. Therefore, when the electromagnetic field stimulated by the acoustic wave is observed, and a change in the strength of the electromagnetic field is observed, it is understood that the charge distribution has changed, i.e., a concentration of the positively charged particles 3 or a concentration of the negatively charged particles 4 has changed, or both of them have changed. As a result, it is possible to measure property values of the charged particles in the measurement object 90, which is the change in concentration of the charged particles in this case, by measuring the electromagnetic field stimulated by the acoustic wave.

Incidentally, FIG. 2 illustrates an example of measuring the change in the concentration of the charged particles by measuring the electromagnetic field that is stimulated by the acoustic wave. However, as the change in the property values of the charged particles that can be measured, it is possible to measure not only a change in the concentration, but also a change in mass, size, shape, the number of charged particles, or a change in interactive force with a medium surrounding the charged particles. For example, based on the other knowledge about a state of the measurement object 90 or the knowledge made available by any other means, the change in strength of the measured electromagnetic field can be coupled to a change in an interactive force with a medium surrounding the charged particles in a state in which changes in concentration, mass, size, shape, and the number of charged particles cannot be caused. Accordingly, for example, the measured change in strength of the electromagnetic field can be coupled to a change in electronic polarizability or positive ion polarizability.

In the property measuring device 100 and the property measuring method according to this embodiment, an electric field, a dielectric constant, or a spatial gradient of an electric field or a dielectric constant can be measured as the electrical property of the measurement object 90. Further, in the property measuring device 100 and the property measuring method according to this embodiment, it is also possible to measure magnetization caused by electron spin or nuclear spin as the magnetic property of the measurement object 90. Specifically, as in the case of the electric polarization, the electromagnetic field is generated even when the magnetization temporally changes. According to the Maxwell equations, the emitted electric field is proportional to the two-time differential of the magnetization time (see Non-Patent Document 1). Accordingly, it is possible to measure the magnitude and the direction of the magnetization from the strength and the phase of the electromagnetic field.

In the property measuring device 100 and the property measuring method according to this embodiment, it is also possible to measure the acoustic magnetic resonance caused by the electron spin or nuclear spin as the magnetic property of the measurement object. Specifically, because the acoustic wave is efficiently absorbed and the direction of the electron spin or the nuclear spin changes at a specific resonance frequency, a large change in the electromagnetic field strength and the phase can be expected at such a frequency. As information, it is possible to ascertain the resonance frequency. In addition, as in the case of normal ESR (Electron Spin Resonance) and NMR (Nuclear Magnetic Resonance), a spectrum is obtained by scanning the frequency of the acoustic wave, and information about the electron spin and the nuclear spin can be acquired. Furthermore, relaxation times of the electron spin and the nuclear spin can be measured.

In the property measuring device 100 and the property measuring method according to this embodiment, a piezoelectric property or a magnetostriction property as the electromechanical property or the magnetomechanical property of the measurement object 90 can be measured as described below. An ion crystal without having an inversion symmetry causes the electric polarization in principle by distortion. Therefore, it is possible to obtain a magnitude of the polarization from a strength of the electromagnetic field of the measurement object which may be called as an acoustically stimulated electromagnetic field. By scanning the acoustic wave, the piezoelectric property of the measurement object 90 can be visualized by imaging. Furthermore, it is possible to measure, in a non-contact manner, piezoelectric tensor from an acoustic wave propagation direction and an angular distribution of the generated electromagnetic field without providing an electrode in the measurement object 90.

In the property measuring device 100 and the property measuring method according to this embodiment, the magnetostriction property can be measured as described below as the electromechanical property or the magnetic mechanical property of the measurement object 90. The magnetosniction is a phenomenon in which an electron orbit is changed by the crystal distortion, and a change is added to the electron spin magnetization through interaction between the orbit and the spin. As another aspect, a magnetic domain is changed by an external distortion, and as a result effective magnetization in a macroscopic region (a size of about an acoustic wave beam spot) may change. Further, a change is caused in crystal field splitting by the crystal distortion, which changes the state of electron and may change the magnitude of the electron spin magnetization. The temporal changes are considered to cause the electromagnetic field. Accordingly, the magnitude of the magnetization, interaction between the orbit and spin, the crystal distortion and sensitivity of the change in electron orbit, crystal field splitting and the sensitivity of the distortion, the relationship between the crystal field splitting and the state of the electron spin, or the relationship between the magnetic domain structure and the distortion can be determined based on the strength of the acoustically stimulated electromagnetic field. The magnetostriction tensor can be measured in a non-contact manner without providing an electrode in the measurement object 90 based on the acoustic propagation direction and the emitting strength. The imaging of the magnetostriction is also possible as in the case of the piezoelectric property.

In the property measuring device 100 and the property measuring method according to this embodiment, the measurement object 90 is irradiated with the acoustic wave, and the electromagnetic field generated by the measurement object 90 is measured. Then, based on at least one type of measurement selected from a group consisting of the strength, the phase, and the frequency of the electromagnetic field, it is possible to extract at least one type of properties selected from a group consisting of the electric property, the magnetic property, the electromechanical property, and the magnetomechanical property of the measurement object 90. Accordingly, as the electrical property of the measurement object 90, it is possible to measure a change of at least type of property values selected from a group consisting of the electric field, the dielectric constant, the spatial gradient of the electric field or the dielectric constant, and the concentration, the mass, the size, the shape, the number of charges of the charged particles of the particles included in the measurement object 90, and the interaction with a medium surrounding the charged particles. As the magnetic property of the measurement object 90, it is possible to measure magnetization caused by the electron spin or the nuclear spin of the measurement object 90, and the acoustic magnetic resonance caused by the electron spin or nuclear spin of the measurement object 90. As the electromechanical property and the magnetomechanical property of the measurement object 90, the piezoelectric property or the magnetostriction property of the measurement object 90 can be measured.

As described above, in the property measuring device 100 according to this embodiment, the electromagnetic field including a measurement object signal generated by the measurement object 90 is received by the receiver 50. The receiver 50 according to this embodiment includes an antenna 52, a band-pass filter 56, and a second amplifier 54. Here, the electromagnetic field generated (emitted) by the measurement object 90 can be measured by measuring the electromagnetic field in a near field, or a non-near field which is not the near field, i.e., a far field. In addition, the type of the antenna 52 is not restricted as long as the electromagnetic field can be detected. For example, a various type of antenna such as a loop antenna or array antennas, or an antenna formed of a loop coil or array coils can be used.

The electromagnetic field received by the antenna 52 is amplified by the second amplifier 54, and thereafter the electromagnetic fields outside a predetermined frequency band (in this embodiment, 9.9 MHz to 10.1 MHz) are removed by the band-pass filter 56.

Then, a third configuration portion of the property measuring device 100 according to this embodiment is a measuring portion 60 for extracting, from an electromagnetic field of a predetermined frequency band formed by the receiver 50, at least one type of properties selected from a group consisting of the electrical property, the magnetic property, the electromechanical property, and the magnetomechanical property of the measurement object 90 as described above.

The measuring portion 60 according to this embodiment first synthesizes a high-frequency waveform which is sent from the first waveform generator 10 through the distributor 15 and whose phase has been adjusted by a phase shifter 62 with the electric signal based on the aforementioned electromagnetic field by a second mixer (in this embodiment, DBM (Double-Balanced Mixer 64. Then, after a low-frequency component (in this embodiment, a frequency component of 1.9 MHz or lower) is extracted by a low-pass filter 66 from the synthesized electric signal, an electric signal to be measured is extracted from the extracted electric signal in a lock-in amplifier 68.

Here, a description will be given of a measurement detail and a specific result thereof.

Figure 3:
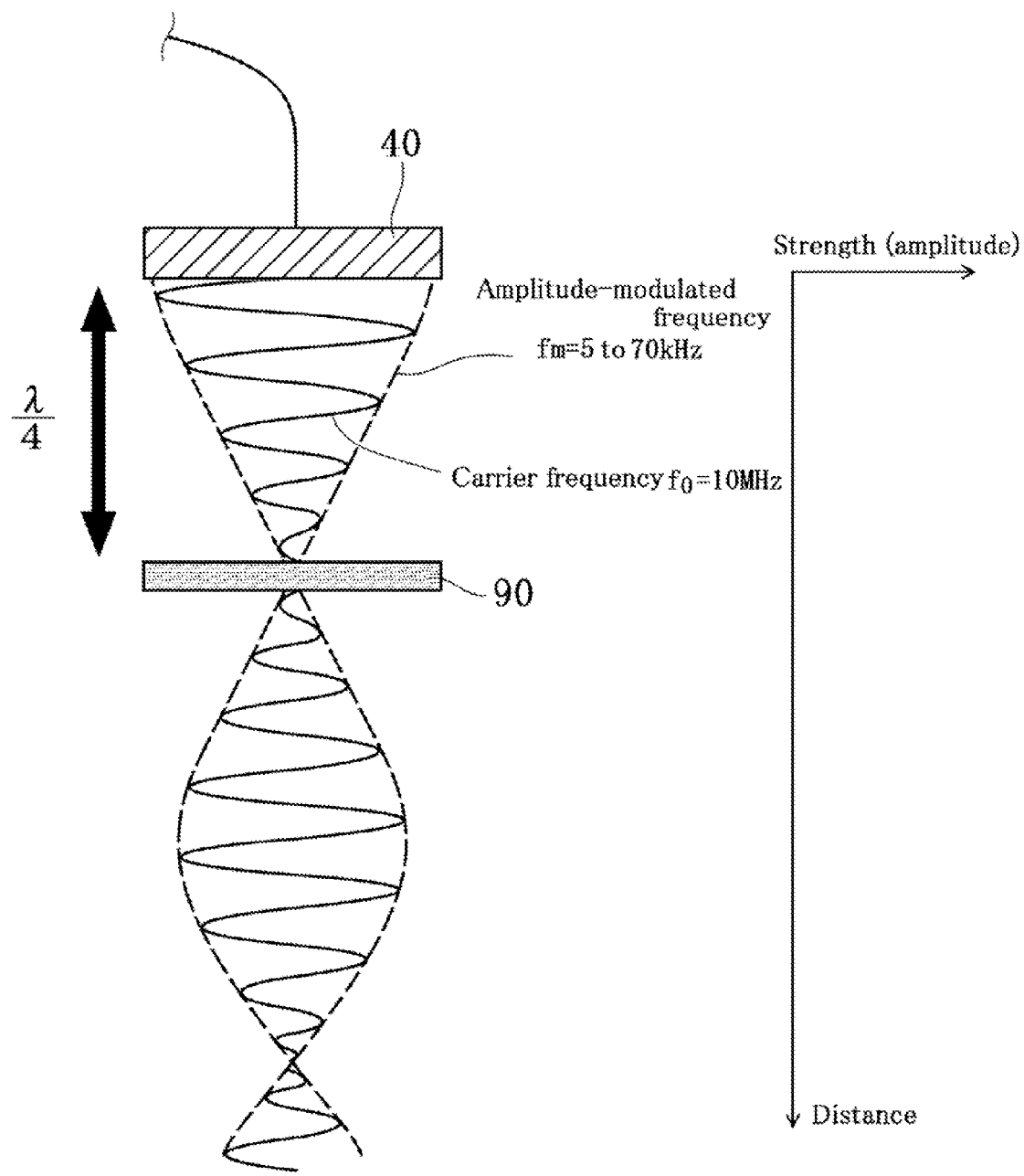
FIG. 3 is a conceptual diagram depicting a relationship between an acoustic wave generator and the measurement object in the property measuring device for measuring the measurement object according to the first embodiment of the present invention.
Figure 4:
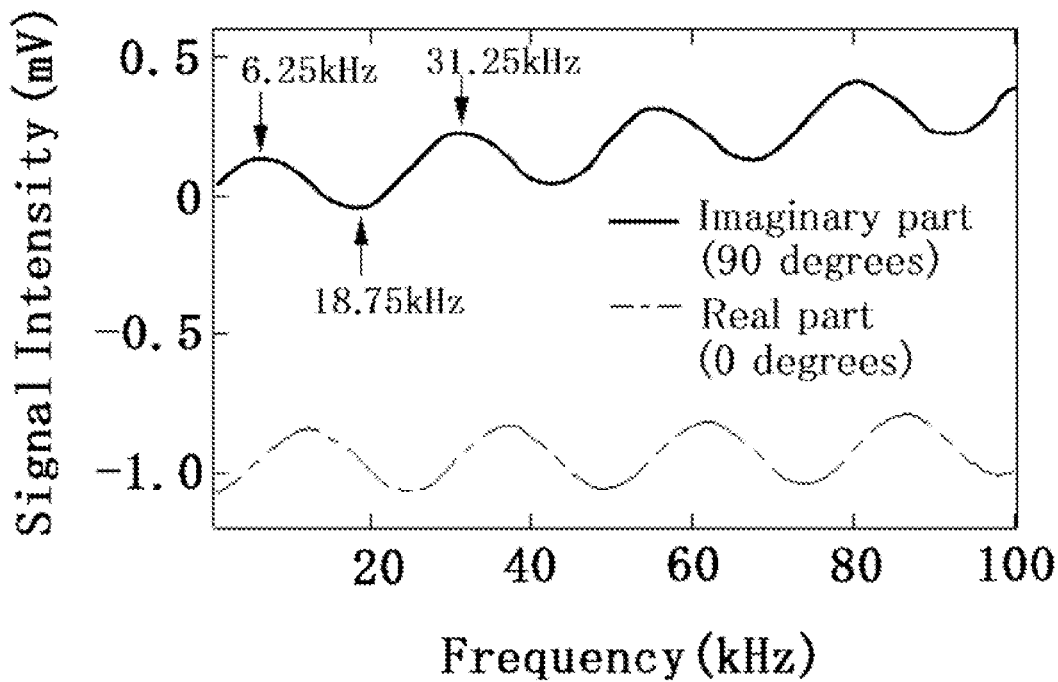
FIG. 4 is a graph indicating a change of a strength (vertical axis) of a signal to be measured (electric signal) by sweeping an amplitude-modulated frequency (horizontal axis) according to the first embodiment of the present invention.

FIG. 3 is a conceptual diagram depicting a relationship between the acoustic wave generator 40 and the measurement object 90 in the property measuring device 100 for measuring the measurement object according to this embodiment. In addition, FIG. 4 is a graph indicating a change of a strength (vertical axis) of a signal to be measured (electric signal) by sweeping an amplitude-modulated frequency (horizontal axis) according to this embodiment. Here, in the graph of FIG. 4, the signal to be measured is indicated as "Imaginary part (90 degrees)".

As illustrated in FIG. 3, the acoustic wave generated by the acoustic wave generator 40 is amplitude-modulated. In this embodiment, the high-frequency component has a carrier frequency ($f_0$) of 10 MHz, and the amplitude-modulated frequency ($f_m$) is a frequency (e.g., 5 kHz to 70 kHz) lower by at least one digit than the carrier frequency. For this reason, when a distance between the acoustic wave generator 40 and the measurement object 90 is the odd integral multiple of the ¼ wavelength, the phase of the noise component generated by the acoustic wave generator 40 and the phase of the electromagnetic field to be measured which is generated by the measurement object 90 are deviated by ideally 90 degrees from each other, as illustrated in FIG. 4. To be more specific, a place where the waveform indicated by 6.25 kHz in FIG. 4 becomes maximum is a place of one-fold of the ¼ wavelength, and a place where the waveform indicated by 18.75 kHz becomes minimum is a place of three-fold of the ¼ wavelength.

Therefore, in this embodiment, by performing, by the lock-in amplifier 68, lock-in detection on a signal (in this embodiment, a waveform generated by the second waveform generator 20) input to the acoustic wave generator 40 as a reference signal, a noise component which is a 0-degree component (real number component) from the acoustic wave generator 40 can be separated from the electric signal to be measured which is a 90-degree component (imaginary number component). To state it differently, the measuring portion 60 of the property measuring device 100 for measuring a measurement object according to this embodiment can highly reliably extract the electric signal to be measured from the electric signal including a noise component from the acoustic wave generator 40. Accordingly, at least one type of properties selected from a group consisting of the electric property, the magnetic property, the electromechanical property, and magnetomechanical property of a portion to be measured of the measurement object 90 can be appropriately extracted.

Here, in this embodiment, the high-frequency component has a carrier frequency ($f_0$) of 10 MHz, which determines the spatial resolution. In contrast, the amplitude-modulated frequency ($f_m$) is a frequency (e.g., 5 kHz to 70 kHz) lower by at least one digit than the carrier frequency. Therefore, in this embodiment, since a frequency lower by three digits or more than the carrier frequency is adopted as the amplitude-modulated frequency, it is possible to highly reliably extract the electric signal to be measured from the electromagnetic noise or the like generated by the acoustic wave generating source. At the same time, according to a property measurement program in this embodiment, since the carrier frequency is a high frequency of 10 MHz, it is possible to maintain a sufficient spatial resolution.

It is interesting to note that, in this embodiment, whether the acoustic wave emitted to the measurement object 90 should be a continuous wave or a pulsed wave is not questioned. This is because it is not necessary to temporally separate the noise generated by the acoustic wave generator 40 and the electric signal to be measured from the measurement object 90 from each other in this embodiment. Emitting the continuous acoustic wave not only makes it easy to extract the electromagnetic field generated by the measurement object 90 but also noticeably increases a time taken for effectively integrating the signal. As a result of this, the S/N ratio remarkably improves, and the measurement time when the continuous wave is emitted can notably reduced as compared with the measurement time when the pulsed acoustic wave is emitted. To state it differently, it is a preferable aspect in view of the foregoing to irradiate the measurement object 90 with a modulated continuous acoustic wave, and receive the modulated continuous acoustic wave by the receiver 50.

For example, in this embodiment, it has been confirmed that the S/N ratio of the continuous wave is improved by 50 times or more as compared with that of the pulsed wave having a half-cycle rectangular pulse (width of 50 ns). To state it differently, it is possible to provide a remarkable effect of reducing the measurement time to about 1/2500 or more than that. In addition, when the continuous acoustic wave is emitted, it is not possible to receive the electromagnetic field including an unnecessary frequency component (e.g., an electromagnetic field noise generated by the pulsed acoustic wave) is observed in emitting a pulsed acoustic wave. Therefore, also in this respect, this makes a contribution to improvement of the S/N ratio. The aforementioned effect provided by emitting the continuous acoustic wave and receiving by the receiver 50 the electromagnetic field generated when the measurement object 90 is irradiated with the continuous acoustic wave can also be provided not only in the case of the amplitude modulation acoustic wave but also in the case of the frequency-modulated acoustic wave as describe later.

Furthermore, as illustrated in FIG. 4, when the amplitude-modulated frequency is swept, the signal strength just corresponding to the odd integral multiple of the ¼ wavelength is expected to be maximum or minimum. As a result, even in the case where the distance between the acoustic wave generator 40 and the measurement object 90 is unclear, it is possible to easily calculate the distance from the acoustic wave generator 40 to the measurement object 90 by finding the frequency at which the signal strength becomes maximum or minimum. For example, when a "condition for obtaining an extreme voltage" is applied to the graph illustrated in FIG. 4, n=1, and the maximum value at 6.25 kHz is represented by $f_{mod}=(v/4d)$. In addition, n=2, and the minimum value at 18.75 kHz is represented by $f_{mod}=(3v/4d)$. Further, n=3, and the maximum value at 6.25 kHz is represented by $f_{mod}=(5v/4d)$. As a result, in the property measuring device 100 for measuring the measurement object of this embodiment, the distance from the acoustic wave generator 40 to the measurement object 90, which was unclear in the beginning, can be measured.

Incidentally, as already described, as one example of the embodiment, the controller for controlling each configuration portion of the property measuring device 100 is connected to the computer. The computer monitors or systematically controls the process of each configuration portion by the property measuring program for the measurement object 90 for executing the process of each configuration portion described above. Hereinafter, the property measuring program for the measurement object 90 will be described with reference to a specific property measuring flowchart. Here, according to this embodiment, the aforementioned property measuring program is stored in a hard disk drive in the computer or a publicly known storage medium such as an optical disc inserted into an optical disc drive or the like provided in the computer. However, the location for storing the property measuring program is not restricted to this. For example, part or whole of the property measuring program may be stored in the controller in this embodiment. In addition, the property measuring program can also monitor or control each process through a publicly known technique such as a local area network or the Internet connection.

Here, in this computer, when the predetermined time of the time-series signal of the acoustically stimulated electromagnetic field is subjected to Fourier transformation using the algorithm of the fast Fourier transformation (FFT), the time required for calculation can be shortened. The means for obtaining the Fourier spectrum may be a computer-independent dedicated DSP (Digital Signal Processor) or FFT device. Also, in the property measuring device 100 in this embodiment, an integrated circuit or a DSP for the receiver 50 can be adopted for signal processing such as amplification and demodulation of the electric signal.

Figure 5:
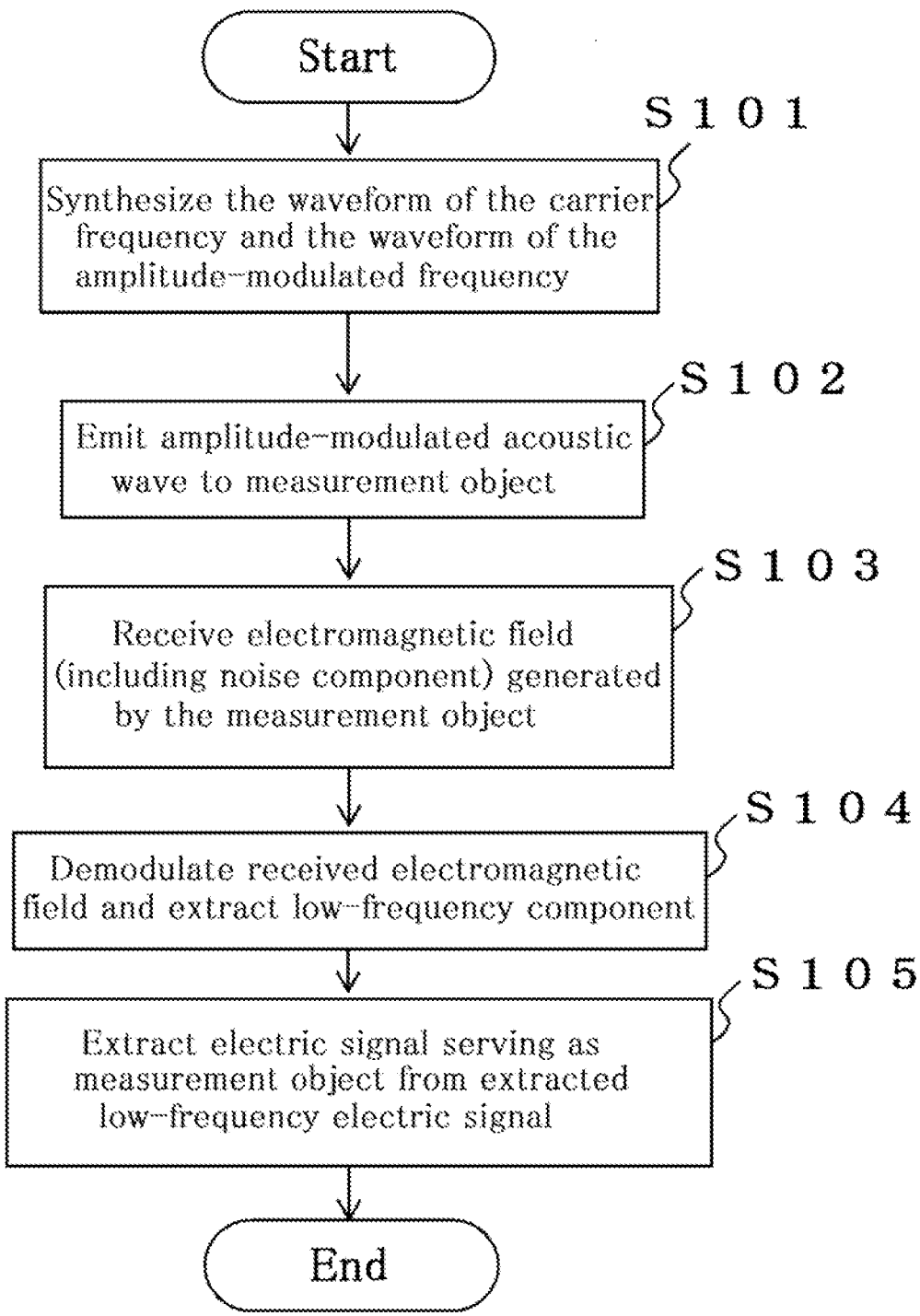
FIG. 5 is a flowchart for measuring the property of the measurement object according to the first embodiment of the present invention.

First, the property measuring program for the measurement object 90 in this embodiment will be described. FIG. 5 is a flowchart for measuring the properties of the measurement object 90 in this embodiment.

As illustrated in FIG. 5, when the property measuring program for measuring a measurement object according to this embodiment is executed and, first, when the measurement object 90 is arranged, the waveform of the carrier frequency and the waveform of the amplitude-modulated frequency are synthesized together in step S101. Therefore, according to this embodiment, in step S101, the waveform of a high-frequency wave of 10 MHz and the waveform of a low-frequency wave of 5 kHz to 70 kHz are synthesized together. Next, in step S102, an emitting process in which the acoustic wave generator 40 emits the amplitude-modulated acoustic wave to the measurement object 90 is performed. Thereafter, in step S103, a receiving step in which the receiver 50 receives the electromagnetic field generated by the measurement object 90 is performed. As described above, this electromagnetic field includes the noise component from the acoustic wave generator 40 and the other noise components.

Next, in step S104, the measuring portion 60 demodulates an electric signal based on the received electromagnetic field (including a noise component) while the carrier frequency serves as a reference, and extracts a low-frequency component through the low-pass filter 66. Thereafter, in step S105, the measuring portion 60 extracts, from the extracted electric signal, an electric signal to be measured which is discriminated from the noise component. According to this embodiment, steps S104 and S105 chiefly correspond to the measuring step.

Accordingly, when the property measuring program according to this embodiment is executed, since the acoustic wave to be emitted to the measurement object 90 is an amplitude-modulated acoustic wave, extraction of the electromagnetic field generated by the measurement object 90 becomes easier as compared with the case where the acoustic wave is not amplitude-modulated. In particular, in this embodiment, since a frequency lower by at least one digit than the carrier frequency is adopted as the amplitude-modulated frequency, it is possible to highly reliably extract the electric signal to be measured from the electromagnetic field noise or the like generated by the acoustic wave generating source. At the same time, according to the property measuring program of this embodiment, since the carrier frequency is a high frequency of 10 MHz, a sufficient spatial resolution can be maintained.

Second Embodiment

A property measuring device 200 for measuring a measurement object (hereinafter, simply referred to as "property measuring device 200") of this embodiment is the same as that in the first embodiment except that the receiver 50 of the first embodiment is changed to a receiver 70. Therefore, a description overlapping the description of the first embodiment can be omitted.

Figure 6:
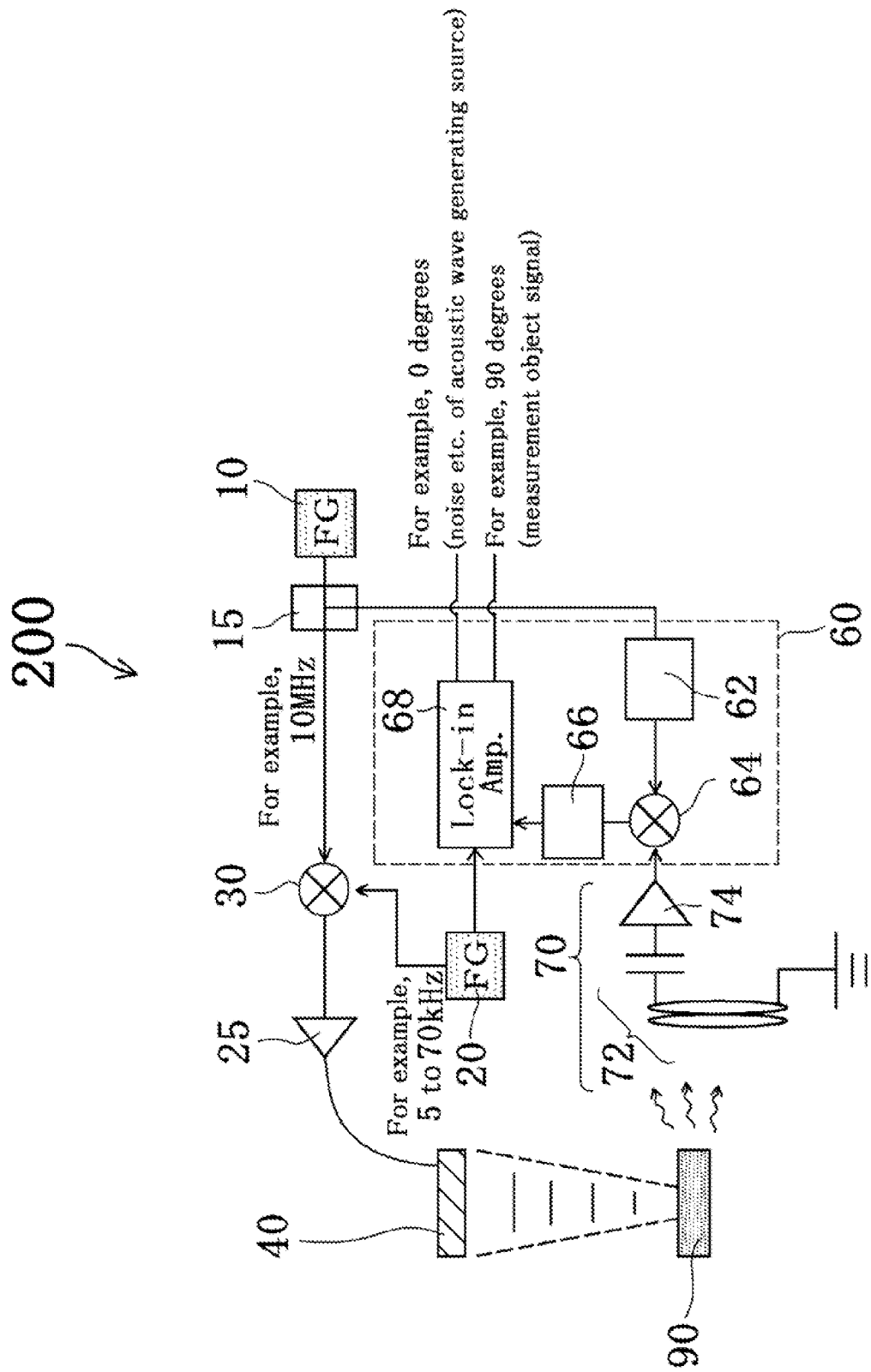
FIG. 6 is a configuration diagram of a property measuring device for measuring a measurement object according to a second embodiment of the present invention.

FIG. 6 is a diagram illustrating a configuration of the property measuring device 200 for measuring a measurement object according to this embodiment. In this embodiment, when the measurement object 90 receives an amplitude-modulated acoustic wave from an acoustic wave generator 40, an electromagnetic field generated by the measurement object 90 is received by a resonance circuit 72 of the receiver 70, and thereafter is sent to a second mixer 64 through an amplifier 74.

Also, even in the case where the property measuring device 200 is adopted after the electromagnetic field generated by the measurement object 90 is received by the receiver 70, it is possible to highly reliably extract, by a measuring portion 60, the electric signal to be measured from the electromagnetic field noise or the like generated by the acoustic generating source.

Third Embodiment

A property measuring device 300 for measuring a measurement object (hereinafter, simply refereed to as "property measuring device 300") in this embodiment is the same as that in the first embodiment except that the receiver 50 of the first embodiment is changed to a receiver 80. Therefore, a description overlapping the description of the first embodiment can be omitted.

Figure 7:
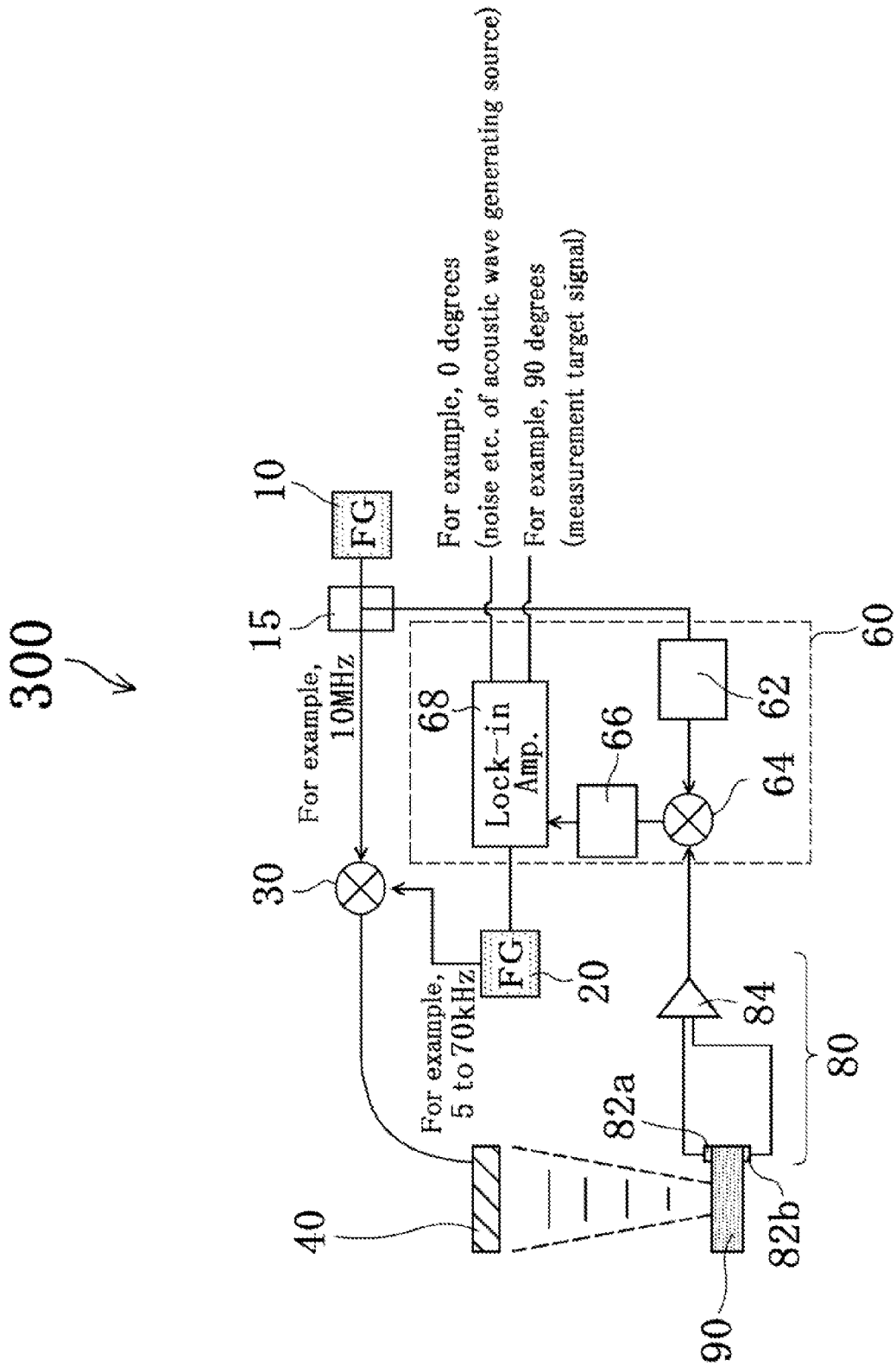
FIG. 7 is a configuration diagram of a property measuring device for measuring a measurement object according to a third embodiment of the present invention.

FIG. 7 is a diagram illustrating a configuration of the property measuring device 300 for measuring a measurement object according to this embodiment. In this embodiment, when the measurement object 90 receives an amplitude-modulated acoustic wave from an acoustic wave generator 40, an electromagnetic field generated by the measurement object 90 is sent from a front surface electrode 82a and a back surface electrode 82b arranged on the measurement object 90 to a second mixer 64 through a wire and an amplifier 84.

Even in the case where the property measuring device 300 is adopted, after the electromagnetic field generated by the measurement object 90 is received by the receiver 80, it is possible to highly reliably extract, by a measuring portion 60, the electric signal to be measured from the electromagnetic field noise or the like generated by the acoustic generating source. Here, the property measuring device 300 of this embodiment is not provided with the band-pass filter 56 which is adopted in the property measuring device 100 of the first embodiment. However, for example, in the case where any particularly large noise does not intrude in a band close to the carrier frequency, or in the case where the electric signal to be measured is sufficiently large, the effect similar to or at least part of that of the first embodiment can be provided even without the band-pass filter 56.

In this embodiment, the magnetic field in the electromagnetic field from the measurement object 90 may be measured using an SQUID (Superconducting Quantum Interference Device). The SQUID is a device including one or two Josephson junctions in a ring formed of a superconductor. In the case where there is one Josephson junction, it is called an rf-SQUID, and in the case where there are two Josephson junctions, it is called a de-SQUID. The SQUID is a super-sensitive magnetic sensor to which a quantization phenomenon of superconduction is applied, has a sensitivity of 100 times higher or more as compared with a conventional magnetic sensor, and is excellent in capable of detecting an extremely small magnetic field such as 1/50,000,000 times or smaller than the earth magnetism.

Further, in the individual embodiments described above, the carrier frequency ($f_0$) is 10 MHz or lower, and the amplitude-modulated frequency ($f_m$) is 5 kHz or higher and 70 kHz or lower. However, the values in this embodiment are not restricted to such frequencies. For example, if the earlier frequency of the acoustic wave generator 40 is 0.1 MHz or higher and 100 MHz or lower, and the amplitude-modulated frequency of the acoustic wave generator 40 is lower by one digit or more than the carrier frequency and at the same time is 0.1 kHz or higher and 100 kHz or lower, it is possible that the same effect or at least part thereof is provided as in the cases of the aforementioned individual embodiments. However, in view of enhancing the applicability as a non-destructive inspection, a preferable range of the carrier frequency is 1 MHz or higher and 20 MHz or lower, and a preferable range of the amplitude-modulated frequency ($f_m$) is 100 kHz or higher and 2000 kHz or lower.

Further, in the individual embodiments described above, although the measuring portion 60 includes the phase shifter 62, the configurations of the individual property measuring devices 100, 200, and 300 described above are not restricted to such a measuring portion. For example, even if the individual property measuring devices 100, 200, and 300 do not include the phase shifter 62, it is possible that the same effect or at least part thereof is provided as in the cases of the aforementioned individual embodiments when a length of a cable is adjusted.

Further, although two waveform generators are adopted in the individual embodiments described above, it is also one of the other aspects which can be adopted to use a single unit of the publicly known waveform generator having both the functions of the first waveform generator 10 and the second waveform generator 20.

In addition, according to the individual embodiments described above, in the lock-in amplifier 68, the electric signal to be measured is extracted from the electric signal including the noise component from the acoustic wave generator 40 by extracting the electric signal of a 90-degree component (imaginary number component). However, the individual embodiments described above are not restricted to such an angle. For example, whole or at least part of the effect provided in the aforementioned individual embodiments can be provided when an angle different from 90 degrees is adopted in accordance with a phase depending on the performance of the property measuring device actually used, part thereof, or the electronic component which constitutes part of the device. Further, an angle different from 90 degrees can be arbitrarily adopted depending on the measurement accuracy required for the measurement object. Accordingly, in the individual embodiments described above, when the electric signal whose angle is deviated by a predetermined angle from a phase of the acoustic wave generated by the acoustic wave emitting portion is extracted as the electric signal to be measured, the predetermined angle is typically 90 degrees. However, the angle is not restricted this.

Other Embodiment

Further, in the individual embodiments described above, the measurement object 90 is irradiated with the amplitude-modulated acoustic wave. However, the effect similar to the foregoing can be provided even in the case where a frequency-modulated acoustic wave is emitted instead of the amplitude-modulated acoustic wave. Hereinafter, a detailed description will be given. In the present application, the frequency modulation may be simply expressed as FM.

Figure 8:
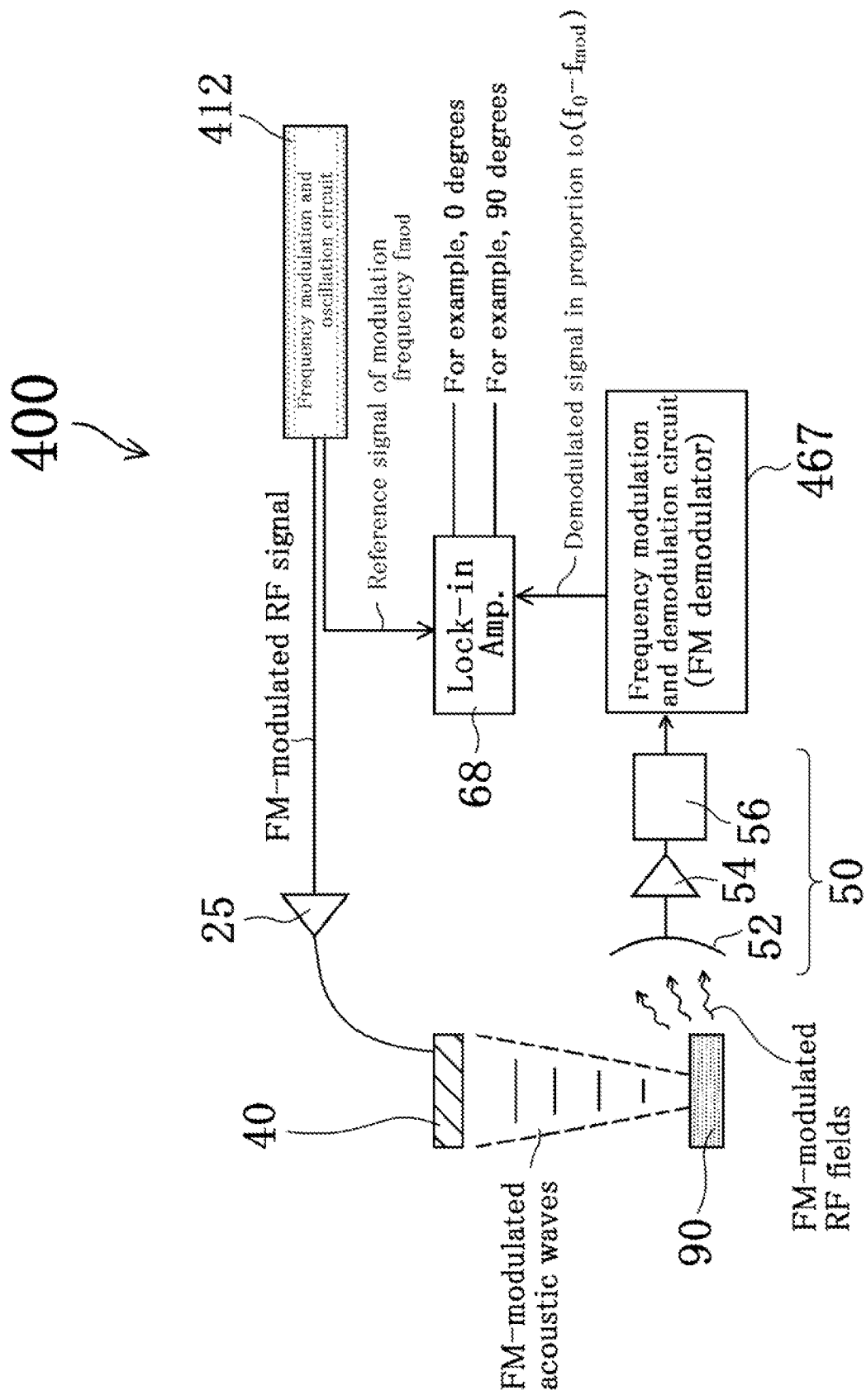
FIG. 8 is a configuration diagram of a property measuring device for measuring a measurement object according to other embodiment of the present invention.

FIG. 8 is a diagram illustrating a configuration of a property measuring device 400 (hereinafter, simply referred to as "property measuring device 400") for measuring a measurement object of this embodiment, by using a frequency-modulated acoustic wave. In addition, FIG. 9 is a conceptual diagram depicting a relationship between an acoustic wave generator 40 and a measurement object 90 in the property measuring device 400 for measuring a measurement object according to this embodiment.

As illustrated in FIG. 8, the property measuring device 400 according to this embodiment is largely divided into three configuration portions.

First, one of the configuration portions is a frequency modulation and oscillation circuit 412 for generating an acoustic wave to be emitted to the measurement object 90. In this embodiment, the frequency of the acoustic wave that is emitted is modulated. Specifically, the frequency is modulated by the modulation frequency (also referred to as a signal wave) ($f_{mod}$) of the frequency modulation with respect to the carrier frequency (the frequency is 10 MHz in this embodiment, but can be largely varied in accordance with the measurement object) ($f_0$). In this case, a wave (f(t)) modulated by the frequency modulation and oscillation circuit 412 is expressed by the following equation.

$$f(t)f_0+f_1 \cos(2\pi f_{mod}+\theta) \quad \text{[Equation 1]}$$

Here, ($f_1$) represents a maximum frequency shift.

After the electric signal subjected to the frequency modulation by the frequency modulation and oscillation circuit 412 is amplified by a first amplifier 25, an acoustic wave which has been subjected to the frequency modulation is emitted toward the measurement object 90 by the acoustic wave generator 40 as illustrated in FIG. 9. As in the case of the amplitude modulation, the acoustic wave emitting portion of this embodiment only refers to the acoustic wave generator 40 in a narrow sense. However, the acoustic wave emitting portion of this embodiment includes the frequency modulation and oscillation circuit 412 in addition to the acoustic wave generator 40 in a broad sense.

Next, a second configuration portion is a receiver 50 for receiving an electromagnetic field generated by the measurement object 90 by being irradiated with the acoustic wave which has been amplitude-modulated. The receiver 50 functions in the same manner as in the case of the first embodiment, and therefore the description thereof will not be repeated.

Then, a third configuration portion of the property measuring device 400 of this embodiment is a measuring portion for extracting one type of properties selected from a group consisting of the electric properly, the magnetic property, the electromechanical property, and the magnetomechanical property of the measurement object 90 from the electric signal in a predetermined frequency band formed by the receiver 50.

In the measuring portion of this embodiment a frequency modulation and demodulation circuit 467 illustrated in FIG. 8 demodulates the electric signal received by the receiver 50 with the carrier frequency ($f_0$) serving as a reference. The demodulated signal is sent to the lock-in amplifier 68 as a demodulated signal which is in proportion to ($f_0-f_{mod}$). In contrast, a reference signal (reference signal having a modulation frequency of $f_{mod}$) to be compared with the demodulated signal is also sent to the lock-in amplifier 68. Then, the electric signal serving as a measurement object is extracted from the electric signal thus extracted in the lock-in amplifier 68.

As described above, in the property measuring device 400 of this embodiment, even in the case where the frequency-modulated acoustic wave is adopted, as in the case of the property measuring device 100 and the property measuring method thereof according to the first embodiment, it is possible to extract at least one type of properties selected from a group consisting of the electric property, the magnetic property, the electromechanical property, and the magnetomechanical property of the measurement object 90 in a non-destructive manner.

Particularly, when the frequency-modulated acoustic wave is adopted, it can be said that it is superior in removing so-called external disturbance (noises and the like) as compared with the case where the amplitude-modulated acoustic wave is adopted, and therefore the property measuring device 400 of this embodiment is one preferable aspect.

Incidentally, as in the case of the property measuring device and the property measuring method for measuring a measurement object using the amplitude-modulated acoustic wave, any of the carrier frequency ($f_0$), the modulated frequency ($f_{mod}$) of the frequency modulation, and the maximum phase shift ($f_1$) in the property measuring device and the property measuring method for measuring a measurement object using the frequency-modulated acoustic wave are not restricted to any specific values, either. A person skilled in the art can arbitrarily change the individual frequencies and the shift described earlier based on the technique explicitly indicated in the embodiment described above or the technique implicitly indicated and including the publicly known technique.

Further, as in the case of the property measuring device and the property measuring method for measuring a measurement object using the amplitude-modulated acoustic wave, it is also possible to adopt an angle different from 90 degrees when the electric signal is extracted from the lock-in amplifier 68 in the property measuring device and the property measuring method for measuring a measurement object using the frequency-modulated acoustic wave. Even in such a case, whole or at least part of the effect provided in the aforementioned embodiments can be provided. In addition, the SQUID or the measuring portion 60 described for the property measuring device and the property measuring method for measuring a measurement object using the amplitude-modulated acoustic wave, or the modified example relating to the waveform generator, can also be applied to the property measuring device and the property measuring method for measuring a measurement object using the frequency-modulated acoustic wave.

It should be noted that the individual embodiments disclosed above are described for explaining the embodiments, but not for restricting the present invention. In addition, a modified example within a scope of the present invention and including the other combination of the individual embodiments is also included in the scope of the claims.

Industrial Applicability

According to the property measuring device, the property measuring method, and the property measuring program for measuring a measurement object of the present invention, it is possible to extract at least one type of properties selected from a group of consisting of the electric property, the magnetic property, the electromechanical property, and the magnetomechanical property of the measurement object in a non-destructive manner. Accordingly, the present invention can be used in a measuring technique for measuring various properties including a measuring technique in the biotechnology in which any of a colloid solution, a liquid crystal, a solid electrolyte, an ion crystal, a semiconductor, a dielectric, a metal, a magnetic substance, and a magnetic fluid, or an object, a structure, or a functional device including such a composite material is a measurement object.

The invention claimed is:

1. A property measuring device for measuring a measurement object, the device comprising:
    an acoustic wave emitting portion, which in operation, emits an amplitude-modulated or frequency-modulated acoustic wave modulated by a modulated frequency (f mod) satisfying the formula:

$$f_{mod}^n = \left(\frac{2n-1}{4d}\right)v$$
$$\left(\begin{array}{l}\text{where } v: \text{sound speed,}\\ d: \text{distance,} \quad n = 1, 2, \ldots\end{array}\right)$$

where v is a sound speed in a medium between the acoustic wave emitting portion and the measurement object and d is a distance between the acoustic wave emitting portion and the measurement object;
    a receiver for receiving an electromagnetic field generated by the measurement object when the measurement object is irradiated by the acoustic wave; and
    a measuring portion for extracting at least one type of property selected from a group consisting of an electric property, a magnetic property, an electromechanical property, and a magnetomechanical property of the measurement object, based on at least one measurement selected from a group consisting of measurements of a strength, a phase, and a frequency of the electromagnetic field.

2. The property measuring device for measuring a measurement object according to claim 1,
    wherein the acoustic wave emitting portion continuously generates the amplitude-modulated or frequency-modulated acoustic wave.

3. The property measuring device for measuring a measurement object according to claim 2,
    wherein the measuring portion extracts a maximum point or a minimum point of the strength of the electromagnetic field by sweeping a modulated frequency of the amplitude-modulated acoustic wave or a modulated frequency of the frequency-modulated acoustic wave emitted from the acoustic wave emitting portion with respect to an electromagnetic field shifted by a predetermined angle from a phase of the acoustic wave generated by the acoustic wave emitting portion.

4. The property measuring device for measuring a measurement object according to claim 2,
    wherein the receiver receives an electromagnetic field generated when the amplitude-modulated or frequency-modulated acoustic wave which is continuously generated irradiates the measurement object.

5. The property measuring device for measuring a measurement object according to claim 4,
    wherein the receiver includes an SQUID (Superconducting Quantum Interference Device) for detecting an electromagnetic field.

6. The property measuring device for measuring a measurement object according to claim 2, wherein the receiver includes an SQUID (Superconducting Quantum Interference Device) for detecting an electromagnetic field.

7. The property measuring device for measuring a measurement object according to claim 1,
wherein the receiver includes an SQUID (Superconducting Quantum Interference Device) for detecting an electromagnetic field.

8. The property measuring device for measuring a measurement object according to claim 1,
wherein the measuring portion extracts a maximum point or a minimum point of the strength of the electromagnetic field by sweeping a modulated frequency of the amplitude-modulated acoustic wave or a modulated frequency of the frequency-modulated acoustic wave emitted from the acoustic wave emitting portion with respect to an electromagnetic field shifted by a predetermined angle from a phase of the acoustic wave generated by the acoustic wave emitting portion.

9. A property measuring method for measuring a measurement object, the method comprising the steps of:
emitting from an acoustic wave emitting portion an amplitude-modulated or frequency-modulated acoustic wave to the measurement object, the acoustic wave being modulated by a modulated frequency (f mod) satisfying the formula:

$$f_{mod}^n = \left(\frac{2n-1}{4d}\right)v$$

$$\begin{pmatrix} \text{where } v\text{: sound speed,} \\ d\text{: distance, } n = 1, 2, \ldots \end{pmatrix}$$

where v is a sound speed in a medium between the acoustic wave emitting portion and the measurement object and d is a distance between the acoustic wave emitting portion and the measurement object;
receiving an electromagnetic field generated by the measurement object; and
extracting at least one type of property selected from a group consisting of an electric property, a magnetic property, an electromechanical property, and a magnetomechanical property of the measurement object, based on at least one measurement selected from a group consisting of measurements of a strength, a phase, and a frequency of the electromagnetic field.

10. The property measuring method for measuring a measurement object according to claim 9,
wherein the amplitude-modulated or frequency-modulated acoustic wave is a continuous wave.

11. The property measuring method for measuring a measurement object according to claim 10,
wherein an electromagnetic field, which is generated when the measurement object is irradiated with the amplitude-modulated or frequency-modulated acoustic wave which is continuously generated, is received in the step of receiving.

12. The property measuring method for measuring a measurement object according to claim 11,
wherein the step of receiving is performed by an SQUID (Superconducting Quantum Interference Device).

13. The property measuring method for measuring a measurement object according to claim 10,
wherein the extracting step extracts a maximum point or a minimum point of the strength of the electromagnetic field by sweeping a modulated frequency of the amplitude-modulated acoustic wave or a modulated frequency of the frequency-modulated acoustic wave with respect to an electromagnetic field shifted by a predetermined angle from a phase of the acoustic wave generated in the step of emitting.

14. The property measuring method for measuring a measurement object according to claim 10,
wherein the step of receiving is performed by an SQUID (Superconducting Quantum Interference Device).

15. The property measuring method for measuring a measurement object according to claim 9,
wherein the extracting step extracts a maximum point or a minimum point of the strength of the electromagnetic field by sweeping a modulated frequency of the amplitude-modulated acoustic wave or a modulated frequency of the frequency-modulated acoustic wave with respect to an electromagnetic field shifted by a predetermined angle from a phase of the acoustic wave generated in the step of emitting.

16. The property measuring method for measuring a measurement object according to claim 9,
wherein the step of receiving is performed by an SQUID (Superconducting Quantum Interference Device).

17. A property measuring method for measuring a measurement object, the method comprising the steps of:
emitting from an acoustic wave emitting portion an amplitude-modulated or frequency-modulated acoustic wave to the measurement object;
setting a distance between the acoustic wave emitting portion and the measurement object in the emitting step to a distance that is an odd integer multiple of one-fourth wavelength of a modulated frequency of the acoustic wave;
receiving an electromagnetic field generated by the measurement object; and
extracting at least one type of property selected from a group consisting of an electrical property, a magnetic property, and electromechanical property, and a magnetomechanical property of the measurement object, based on at least one measurement selected from a group consisting of measurement of a strength, a phase, and a frequency of the electromagnetic field.

18. The property measuring method for measuring a measurement object according to claim 17, wherein the amplitude-modulated or frequency-modulated acoustic wave is a continuous wave.

19. The property measuring method for measuring a measurement object according to claim 17, wherein the extracting step extracts a maximum point or a minimum point of the strength of the electromagnetic field by sweeping a modulated frequency of the amplitude-modulated acoustic wave or a modulated frequency of the frequency-modulated acoustic wave with respect to an electromagnetic field shifted by a predetermined angle from a phase of the acoustic wave generated in the step of emitting.

* * * * *